United States Patent [19]

Dawson et al.

[11] 4,000,189
[45] Dec. 28, 1976

[54] PHARMACOLOGICALLY ACTIVE PROPANOIC ACID DERIVATIVES

[75] Inventors: William Dawson, Camberley; Michael John Foulis, Bracknell; Norman James Albert Gutteridge, Camberley; Colin William Smith, Bracknell, all of England

[73] Assignee: Lilly Industries, Ltd., London

[22] Filed: Apr. 10, 1974

[21] Appl. No.: 459,831

[30] Foreign Application Priority Data

Apr. 12, 1973  United Kingdom ............ 17735/73

[52] U.S. Cl. .................... 260/515 R; 260/469; 260/471 R; 260/473 A; 260/473 R; 260/470 R; 260/487; 260/488 CD; 260/520 B; 424/308; 424/317
[51] Int. Cl.$^2$ ................. C07C 65/22; C07C 65/20; C07C 65/14
[58] Field of Search .......... 260/515 R, 520 B, 469, 260/476 R, 473 A, 488 H

[56] References Cited

UNITED STATES PATENTS

| | | | |
|---|---|---|---|
| 3,649,678 | 3/1972 | Fusco et al. | 260/501.16 |
| 3,732,267 | 5/1973 | Miyano | 260/413 |
| 3,875,214 | 4/1975 | Schneider | 260/499 |
| 3,888,905 | 6/1975 | Miyano | 260/471 A |

OTHER PUBLICATIONS

Iesen et al., Reagents for Organic Synthesis, pp. 142–143 (1967).

Primary Examiner—Robert Gerstl
Attorney, Agent, or Firm—Steven L. Lammert; James L. Rowe; Everet F. Smith

[57] ABSTRACT

The invention provides styryl cyclopentenyl propanoic acids and derivatives thereof having spasmolytic activity coupled with low toxicity. Also provided is a method of preparing styryl cyclopentenyl propanoic acid compounds which involves cyclising 7-hydroxy-5,8-dioxo-10-phenyldec-9-enoic acid in the presence of a base.

6 Claims, No Drawings

PHARMACOLOGICALLY ACTIVE PROPANOIC ACID DERIVATIVES

This invention relates to novel cyclopentenyl propanoic acids and to a method by which such compounds may be prepared. The novel compounds of this invention possess useful pharmacological activity and accordingly the present invention also provides pharmaceutical compositions comprising one or more of the active compounds of the invention.

According therefore to a first aspect of the present invention, there are provided novel compounds of the formula:

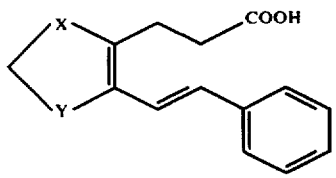

and salts and esters thereof, wherein Y represents >C=O or >CHOR, when Y is >C=O, X represents >C=O and when Y is >CHOR, X represents >C=O or >CHOR, and R represents hydrogen or an acyl or benzoyl group.

Examples of preferred salts of the acids of formula I are the alkali metal salts, particularly the sodium and potassium salts. The nature of the ester function in the esters of the present invention depends on the use to which said esters are to be put. Thus the ester function may be used to alter the absorption and retention characteristics of the parent acid of formula I or merely to protect that acid during conversion thereof to another compound of formula I as illustrated hereinafter. A large number of esters suitable for such purposes are known to those skilled in the art, for example alkyl, haloalkyl, silyl, cycloalkyl, cycloalkyl-alkyl, aralkyl, heteroaryl-alkyl, alkylaminoalkyl and alkoxyalkyl esters, and such esters form a part of this invention. For reasons of cost and ease of production, the preferred esters of the present invention are $C_{1-4}$ alkyl and halo-$C_{1-4}$ alkyl esters such as the methyl, ethyl, n-propyl, isobutyl, t-butyl, chloromethyl, trifluoromethyl, 2-chloroethyl or 2,2,2-trichloroethyl esters.

When R in formula I above is an acyl or benzoyl group, the preferred examples of such groups are $C_{2-4}$ acyl, $C_{2-4}$-haloacyl, benzoyl, nitrobenzoyl, halobenzoyl, $C_{1-4}$ alkylbenzoyl and $C_{1-4}$ alkoxybenzoyl, and especially acetyl, propionyl, chloroacetyl, 3,3,3-trichloropropionyl, benzoyl, p-nitrobenzoyl, p-methylbenzoyl, p-methoxybenzoyl and p-chlorobenzoyl.

According to a second aspect of the present invention, there is provided a process for preparing the compounds of formula I which comprises the steps of:

a. cyclising a compound of the formula:

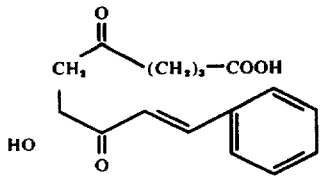

or a salt or ester thereof, in the presence of a base to produce a compound of formula I or a salt or ester thereof in which X is >C=O and Y is >CHOR where R is hydrogen;

b. acylating or benzoylating the resultant compound from step (a) to produce a compound of formula I or a salt or ester thereof in which X is >C=O and Y is >CHOR where R is acyl or benzoyl;

c. oxidising the resultant compound from step (a) to produce a compound of formula I or a salt or ester thereof in which X and Y are >C=O;

d. reducing the resultant compound from step (a) or step (b) to produce a compound of formula I or a salt or ester thereof in which respectively X and Y are >CHOH or X is >CHOH and Y is >CHOR where R is acyl or benzoyl;

e. acylating or benzoylating the resultant compound from step (d) to produce a compound of formula I or a salt or ester thereof in which X and Y are >CHOR where R is acyl or benzoyl;

f. salifying or esterifying a free acid of formula I resulting from any one of steps (a) to (e).

In step (a), the cyclisation proceeds smoothly at room temperature under mild basic conditions, for example using 0.1M sodium hydroxide. The cyclisation reaction is usually complete within about 2 hours.

The starting materials of formula II are novel compounds which may be prepared by reaction of styryl glyoxal and 3-oxoheptane-1,7-dioic acid optionally followed by salification or esterification as is more fully described in the specification of our co-pending U.S. application Ser. No. 459,830 filed concurrently herewith. If desired, the compounds of Formula II need not be isolated but may be cyclised directly to the desired compound of Formula I, the cyclisation being carried out in the reaction medium in which the formula II compound is formed.

Although an ester of the intermediate of formula II may be used, it will be appreciated that partial hydrolysis of the ester will normally occur during the cyclisation. Accordingly, where an ester of the product of step (a) is desired, it is preferably obtained by cyclisation of the free acid of formula II followed by esterification of the resultant cyclised product.

In step (c), the oxidation is normally carried out at low temperatures, at least at the commencement of the reaction. Thus the product from step (a) may be added to the oxidising agent, preferably chromium trioxide, suspended in a suitable solvent such as pyridine at 0° C. The reaction mixture is then stirred for up to 24 hours to complete the reaction, during which time the temperature may be allowed to rise slowly to 20° – 25° C. The desired product is then extracted from the reaction mixture, purified and isolated in conventional manner.

In step (d), the reduction is preferably carried out using a complex metal hydride reducing agent such as sodium or potassium borohydride. The reducing agent is normally added in portions over a period of 1 to 2 hours to a solution of the compound from step (a) or step (b) in a suitable solvent, for example aqueous ethanol, and desirably in the presence of a suitable organic base such as triethylamine. Following completion of the addition of the reducing agent, the reaction is allowed to continue usually for a further 1 to 2 hours before being stopped by acidifying the reaction mixture, for example by addition of dilute aqueous oxalic acid, and the product isolated.

Steps (b) and (e) of the above process involve reaction of the products produced in steps (a) and (d) respectively with an appropriate acylating agent. Such acylation reactions are well known in the art and may be accomplished in conventional manner by reaction with an appropriate acid anhydride such as acetic anhydride, propionic anhydride, 3,3,3-trichloropropionic anhydride or an appropriate acyl halide such as acetyl chloride, benzoyl chloride, p-nitrobenzoyl chloride, and p-chlorobenzoyl chloride.

Similarly step (f) involves conventional salification or esterification of the free acids produced in steps (a) to (e). Thus salts are prepared by reaction of the acid with an appropriate base, for example an alkali metal hydroxide, carbonate or hydrogen carbonate. Esters may be prepared in a variety of well-known ways, preferably by reaction with an appropriate alcohol in the presence of an acid catalyst, for example by reaction with methanol, ethanol, isopropanol, t-butanol, trifluoromethanol and 2,2,2-trichlorothanol in the presence of p-toluene sulphonic acid. In the case of alkyl esters, reaction of the acid with a diazoalkane such as diazomethane or diazoethane may also be conveniently used.

In the starting material of formula II used in the foregoing process, the wavy line ∼ is intended to signify that the hydroxyl group may be in either of the possible configurations and formula II as a whole is meant to represent both enantiomorphs and the racemic mixture thereof. When step (a) of the foregoing reaction sequence is carried out using a optically active compound of formula II, the resultant product and the products of subsequent reaction steps (b), (d), (e) and (f) will also be optically active. More usually, however, the racemic form of the compounds of formula II will be used with the result that the compounds of formula I produced in step (a) will also be in racemic form and those compounds produced in step (d) will be obtained as a mixture of racemates. In the latter case, the individual racemates can be isolated and obtained in pure form from the mixture by the usual means, for example by repeated crystallisation from suitable solvents.

If desired, the individual racemates can be separated into their enantiomorphs in conventional manner, for example by chemical separation and such enantiomorphs as well as the racemates form a part of this invention. Chemical separation may be achieved by forming diastereoisomers from the racemic mixture by reaction with an appropriate optically active separating agent. Thus the free acids of formula I may be reacted with an optically active amine such as (−)-ephedrine or (+)- and (−)-α-methylbenzylamine, the difference in the solubility of the diastereoisomers obtained permitting selective re-crystallisation of one form and regeneration of the optically active acid of formula I from the mixture.

As stated previously the compounds of formula I, whether in racemic or optically active form, and salts and esters thereof possess useful pharmacological activity. More particularly, the compounds of the present invention have been found to possess spasmolytic activity and to have low toxicity such as to render them useful in the treatment of such conditions as bronchial spasm and intestinal colic. This activity has been demonstrated at doses of from 0.1 to 150 mg./Kg. depending on the test procedure used. In the treatment of humans, clinical effects are therefore likely to be seen at doses of from 0.5 to 15 mg./Kg. but, of course, doses outside this range may be used at the discretion of the physician treating the patient. The pharmacologically active compounds of the invention may be administered by the enteral or parenteral routes and for this purpose they will normally be formulated into pharmaceutical compositions comprising the active ingredient in association with at least one pharmaceutically acceptable carrier therefor. Such compositions form a part of this invention and will normally consist of the active ingredient mixed with a carrier, or diluted by a carrier, or enclosed or encapsulated by a carrier in the form of a capsule, sachet, cachet or other container. The carrier may be a solid, semi-solid or liquid material which serves as a vehicle, excipient, coating agent, or medium for the active ingredient. Some examples of the carriers which may be used are lactose, dextrose, sucrose, sorbitol, mannitol, starch, gum acacia, calcium phosphate, liquid paraffin, cocoa butter, oil of theobroma, alginates, tragacanth, gelatin, methyl cellulose, polyoxyethylene sorbitan monolaurate, methyl- or propylhydroxybenzoate, ethyl cellulose acetate phthalate, low viscosity acetyl cellulose acetate, paraffin wax, mineral wax, vegetable wax, vegetable gum, silicone rubbers such as liquid polydimethylsiloxane rubber, plasticised or unplasticised polyvinyl chloride, plasticised polyethylene terephthalate, modified collagen, cross-linked hydrophilic polyether gel, cross-linked polyvinyl alcohol or cross-linked partially hydrolysed polyvinyl acetate.

Advantageously the compositions of the invention are formulated in a dosage unit form containing from 5 to 500 mg. (preferably 10 to 150 mg.) of the active ingredient. Examples of suitable dosage unit forms are tablets, hard or soft gelatin capsules, microcapsules and suppositories as well as drug dispensing systems comprising the active ingredient contained in a flexible, imperforate polymeric material through which the drug may be released slowly by diffusion. More generally, the term "dosage unit form" as used herein means a physically discrete unit containing the active ingredient, generally in admixture with and/or enclosed by a pharmaceutical carrier, the quantity of active ingredient being such that one or more units are normally required for a single therapeutic administration.

The compositions of the present invention will, of course, be adapted to the particular route of administation. Thus, for oral administration, tablets, pills, capsules, solutions or suspensions may be used; for parenteral administration, sterile injection solutions or suspensions may be used; and for rectal administration, suppositories may be used. Any of the foregoing compositions may, of course, be formulated in delayed or sustained release form in a manner well known in the art.

The following Examples will further illustrate the preparation of the novel compounds of this invention:

EXAMPLE 1

7-Hydroxy-5,8-dioxo-10-phenyldec-9-enoic acid (0.20 g.) was dissolved in 0.1M sodium hydroxide (17.5 ml.) at room temperature. The solution was stirred for 45 minutes, acidified with 0.1M hydrochloric acid (19.5 ml.) and extracted with ethyl acetate. The organic phase was washed with brine, dried over anhydrous magnesium sulphate and evaporated to an oil which, on trituration with cold ethyl acetate, yielded white crystals of 3-[3-hydroxy-5-oxo-2-(β-styryl)cyclopent-1-enyl]propanoic acid, m.p. 191° C. Phenyl hy-

EXAMPLE 2

This Example illustrates the cyclisation of 7-hydroxy-5,8-dioxo-10-phenyldec-9-enoic acid in situ in the reaction medium in which it was formed:

2M aqueous sodium hydroxide solution (1.15 l.) was added dropwise over 2 hours to a stirred, ice-cooled solution of diethyl 3-oxoheptane-1,7-dioate (230 g.) (*Organic Syntheses*, 42, 41) in methanol (200 ml.). Stirring at room temperature was continued for three days. The pH of the solution was adjusted to 8 by the addition of solid carbon dioxide, and then styryl glyoxal hemihydrate (169 g.) was added. The mixture was stirred for a further 18 hours. The residual solid was removed by filtration and the filtrate was stirred for 1¼ hours with 1M aqueous sodium hydroxide solution (2 l.). The solution was acidified to pH2 by the addition of 5M hydrochloric acid and the acidic organic products were extracted into ethyl acetate. The extract was washed with water and dried over magnesium sulphate. The solution afforded (on evaporation) a crystalline solid which was collected by filtration and washed with ethyl acetate.

On crystallisation from ethyl acetate, there was obtained 3-[3-hydroxy-5-oxo-2-($\beta$-styryl)cyclopent-1-enyl]propanoic acid, m.p. 188° – 190° C. $\lambda$max (MeOH) 325 mm.; $\epsilon$max 35,800; I.R. 3180, 2660, 2550, 1690, 1670, 758 and 690 $cm^{-1}$.

EXAMPLE 3

The racemic acid prepared in Examples 1 and 2 was resolved as follows:

The ($\pm$)- acid (4 g.) was added to boiling ethyl acetate (200 ml.), solubilised with the minimum of ethanol, and filtered. To this solution was added (−)-$\alpha$-methylbenzylamine (1.8 g.) in ethyl acetate (25 ml.), the solution was stirred until crystals formed and was then chilled for 24 hours. The crystals were re-crystallised twice from ethanol acetate (500 ml. then 450 ml.), and then filtered off, the mother liquors being retained. The crystals were then dissolved in ethyl acetate, shaken with excess 1M hydrochloric acid, washed with a saturated salt solution and dried with sodium sulphate. The solution was filtered, evaporated to small bulk, chilled and filtered to yield (+)-3-[3-hydroxy-5-oxo-2-($\beta$-styryl)cyclopent-1-enyl]propanoic acid, m.p. 212° C., $[\alpha]_D^{21} = +34.0\pm2.0$(EtOH). On re-crystallisation from ethanol, the (+)- acid melted at 216° C., $[\alpha]_D^{21} = +49.0\pm3.0$(EtOH).

The mother liquors mentioned above were evaporated to 400 ml., acidified with 1M hydrochloric acid and the solution worked up as described above to yield (−)-3-[3-hydroxy-5-oxo-2-($\beta$-styryl)cyclopent-1-enyl]propanoic acid, m.p. 208° C., $[\alpha]_D^{21} = -40.0\pm2.4$(EtOH). On re-crystallisation from ethanol, the (−)- acid melted at 216° C., $[\alpha]_D^{21} = -46.0\pm3.0$(EtOH).

The identical procedure was carried out using the ($\pm$)-acid (4 g.) and (+)-$\alpha$-methylbenzylamine (1.8 g.). Initially this gave the (−)-isomer, m.p. 212° C., $[\alpha]_D^{20} = -35.0\pm2.0$(EtOH) and the mother liquors yielded the (+)-isomer, m.p. 210° C., $[\alpha]_D^{22} = +36.0\pm2.0$(EtOH). Re-crystallisation of the (+)-(−)- isomers from ethanol yielded products of the same melting point and optical rotation as those mentioned above.

EXAMPLE 4

Using the procedure of Example 1, but starting with methyl 7-hydroxy-5,8-dioxo-10-phenyldec-9-enoate, there was obtained methyl 3-[3-hydroxy-5-oxo-2-($\beta$-styryl)cyclopent-1-enyl]propanoate, m.p. 80° C.

Alternatively, and preferably, the same ester was prepared by dissolving 3-[3-hydroxy-5-oxo-2-($\beta$-styryl)cyclopent-1-enyl]propanoic acid (6 g.) in methanol (250 ml.) and stirring at room temperature for 20 hours with p-toluene sulphonic acid (50 mg.). The reaction mixture was rotary evaporated to an oil which, on trituration with cold ether, yielded the desired ester. Similarly, by esterifying (+)- or (−)-3-[3-hydroxy-5-oxo-2-($\beta$-styryl)cyclopent-1-enyl]propanoic acid, there were obained respectively the (+)- and (−)-methyl esters.

EXAMPLE 5

Methyl 3-[3-hydroxy-5-oxo-2-($\beta$-styryl)cyclopent-1-enyl]propanoate. (2.0 g.) was dissolved in pyridine (30 ml.) and treated with acetic anhydride (1.65 g.) at room temperature. The reaction mixture was rotary evaporated to an oil which was chromatographed on a silica gel column in ether. The first main fraction was rotary evaporated to an oil which crystallised on treatment with n-hexane to yield methyl 3-[3-acetoxy-5-oxo-2-($\beta$-styryl)cyclopent-1-enyl]propanoate, m.p. 78° – 79° C.

EXAMPLE 6

Methyl 3-[3-hydroxy-5-oxo-2-($\beta$-styryl)cyclopent-1-enyl]propanoate (1.8 g.) was dissolved in pyridine (30 ml.) and treated with p-chlorobenzoyl chloride (1.93 g.) at room temperature. After 2 hours the mixture was filtered and the filtrate rotary evaporated to an oil. Trituration with ether yielded a first crop of pyridine hydrochloride and, on addition of further ether, there was obtained methyl 3-[3-(p-chlorobenzyloxy)-5-oxo-2-($\beta$-styryl)cyclopent-1-enyl]propanoate, m.p. 114° – 115° C.

EXAMPLE 7

3-[3-Hydroxy-5-oxo-2-($\beta$-styryl)cyclopent-1-enyl]-propanoic acid (5.0 g.) was slowly added to an ice cold suspension of chromium trioxide (5.5 g.) in pyridine (50 ml.). The mixture was stirred for 2 hours at 0° C. and then for 16 hours at room temperature. The reaction mixture was poured into water and extracted with ethyl acetate/chloroform (1:1). The organic phase was washed with water, dilute hydrochloric acid, and again water, then dried over anhydrous magnesium sulphate and rotary evaporated to an oil. On treatment of the oil with chloroform/ether, there was obtained 3-[3,5-dioxo-2-[$\beta$-styryl)cyclopent-1-enyl]propanoic acid, m.p. 116° – 117° C. On esterification of this acid with t-butanol or 2,2,2-trichloroethanol in the presence of p-toluene sulphonic acid, there was obtained respectively t-butyl- and 2,2,2-trichloroethyl-3-[3,5-dioxo-2-($\beta$-styryl)cyclopent-1-enyl]-propanoate.

EXAMPLE 8

3-[3-Hydroxy-5-oxo-2-($\beta$-styryl)cyclopent-1-enyl]-propanoic acid (1.0 g.) was dissolved in a mixture of ethanol (18 ml.), water (2 ml.) and triethylamine (0.56 ml.). The solution was stirred at 0° C. and a solution of sodium borohydride (0.14 g.) in water (2 ml.) was added. A second quantity of sodium borohydride (0.14 g.) in water (2 ml.) was added 40 minutes after the first and a third such quantity was added after a further 40 minutes. Eighty minutes after the final addition, the reaction was quenched by the addition of dilute aqueous oxalic acid solution. Water (30 ml.) was added and the pH of the solution was lowered to 4 by addition of further oxalic acid solution. The solution was extracted twice with ethyl acetate and the combined extract was washed twice with a small quantity of saturated aqueous sodium chloride. Drying and evaporation of the extract afforded an oil which yielded a first crop of cyrstals on trituration with ethyl acetate. The crystals were removed by filtration and washed with ethyl acetate. The mother liquor was evaporated to dryness and triturated with chloroform. A second crop of crystals was obtained.

The first crop of crystals was re-crystallised from ethyl acetate to give cis-3-[3,5-dihydroxy-2-($\beta$-styryl)-cyclopent-1-enyl]propanoic acid, m.p. 147° – 148° C.; I.R. $\nu$O-H 3240 cm.$^{-1}$, $\nu$C-O 1060, 1075 cm.$^{-1}$; TLC Rf0.42 (silica gel, CHCl$_3$/MeOH/AcOH 90:10:1).

The second crop of crystals was re-crystallised from methanol/chloroform to yield trans-3-[3,5-dihydroxy-2-($\beta$-styryl)cyclopent-1-enyl]propanoic acid, m.p. 124° – 126° C.; I.R. $\nu$O-H 3250, 3410 cm.$^{-1}$, $\nu$C-O 1040, 1065 cm.$^{-1}$; TLC Rf0.33 (silica gel, CHCl$_3$/MeOH/AcOH 90:10:1).

We claim:

1. A compound selected from the group consisting of
1. the carboxylic acid of the formula

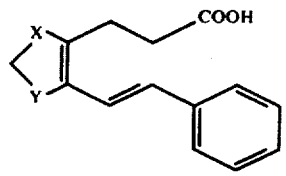

wherein Y and X are the same or different and can each represent >C=O or >CHOR with the proviso that when Y is >C=O, X can only represent >C=O; and wherein R represents hydrogen, $C_{2-4}$ alkanoyl, $C_{2-4}$ haloalkanoyl, benzoyl, nitrobenzoyl, halobenzoyl, $C_{1-4}$-alkylbenzoyl, and $C_{1-4}$-alkoxybenzoyl;
2. its alkali metal salt; or
3. its $C_{1-4}$ alkyl or halo-$C_{1-4}$ alkyl ester.

2. The carboxylic acid according to claim 1.

3. The sodium or potassium salt according to claim 1.

4. A compound of claim 1 said compound being 3-[3-hydroxy-5-oxo-2-($\beta$-styryl)cyclopent-1-enyl]propanoic acid in racemic or optically-active form.

5. A compound of claim 1 said compound being 3-[3,5-dioxo-2-($\beta$-styryl)cyclopent-1-enyl]propanoic acid.

6. A compound of claim 1 said compound being cis-[3,5-dihydroxy-2-($\beta$-styryl)cyclopent-1-enyl]-propanoic acid.

* * * * *